US012673210B2

(12) United States Patent
Campbell et al.

(10) Patent No.: US 12,673,210 B2
(45) Date of Patent: Jul. 7, 2026

(54) ENERGY HARVESTING SYSTEM INTEGRITY MONITORING

(71) Applicant: Medtronic, Inc., Minneapolis, MN (US)

(72) Inventors: Michael P. Campbell, Blaine, MN (US); Richard J. O'Brien, Hugo, MN (US)

(73) Assignee: Medtronic, Inc., Minneapolis, MN (US)

( * ) Notice: Subject to any disclaimer, the term of this patent is extended or adjusted under 35 U.S.C. 154(b) by 747 days.

(21) Appl. No.: 18/059,546

(22) Filed: Nov. 29, 2022

(65) Prior Publication Data

US 2023/0233865 A1 Jul. 27, 2023

Related U.S. Application Data

(60) Provisional application No. 63/267,202, filed on Jan. 27, 2022.

(51) Int. Cl.
*A61N 1/37* (2006.01)
*A61B 5/00* (2006.01)
*A61B 5/363* (2021.01)

(52) U.S. Cl.
CPC .......... *A61N 1/3702* (2013.01); *A61B 5/0006* (2013.01); *A61B 5/0031* (2013.01); *A61B 5/363* (2021.01)

(58) Field of Classification Search
None
See application file for complete search history.

(56) References Cited

U.S. PATENT DOCUMENTS

| | | | |
|---|---|---|---|
| 7,848,811 B2 | 12/2010 | Moon et al. |
| 8,805,530 B2 | 8/2014 | John |
| 9,155,479 B2 | 10/2015 | Solem |
| 9,180,303 B2 | 11/2015 | Goetz |

(Continued)

FOREIGN PATENT DOCUMENTS

| | | |
|---|---|---|
| WO | 2007016781 A1 | 2/2007 |
| WO | 2021154885 A2 | 8/2021 |

OTHER PUBLICATIONS

Beach et al., "Inertial Kinetic Energy Harvesters for Wearables: The Benefits of Energy Harvesting at the Foot", IEEE Access, vol. 8, IEEE, Nov. 2020, pp. 208136-208148.

(Continued)

*Primary Examiner* — Erica S Lee
(74) *Attorney, Agent, or Firm* — Fortem IP LLP

(57) ABSTRACT

A system includes harvester circuitry configured to charge a battery for a medical device using a displacement of a harvester mass, one or more accelerometers configured to detect a motion associated with the harvester mass, and processing circuitry. The processing circuitry is configured to determine, with the one or more accelerometers, motion information for the implanted medical device during a time range that occurs when the harvester circuitry charges the battery using the displacement of the harvester mass. The processing circuitry are further configured to determine a harvester output generated by the harvester circuitry during the time range and output an indication of a potential failure of the harvester mechanism based on the motion information and the harvester output.

21 Claims, 9 Drawing Sheets

(56) References Cited

U.S. PATENT DOCUMENTS

| | | | |
|---|---|---|---|
| 10,773,088 B2 | 9/2020 | Carney et al. | |
| 2003/0014091 A1 | 1/2003 | Rastegar et al. | |
| 2013/0320212 A1 | 12/2013 | Valentino et al. | |
| 2013/0335011 A1* | 12/2013 | Bohringer | H02K 7/1876 |
| | | | 29/831 |
| 2015/0313519 A1 | 11/2015 | McKenna | |
| 2020/0281471 A1* | 9/2020 | Hunter | A61B 5/6812 |
| 2020/0289830 A1 | 9/2020 | Makdissi et al. | |
| 2022/0087604 A1* | 3/2022 | Bailey | A61B 5/1114 |

OTHER PUBLICATIONS

International Search Report and Written Opinion of International Application No. PCT/IB2023/050462 dated Mar. 28, 2023, 12 pp.
Pfenniger et al., "Energy Harvesting from the Cardiovascular System, or How to Get a Little Help from Yourself", Annals of Biomedical Engineering, vol. 41, No. 11, Nov. 2013, pp. 2248-2263.

* cited by examiner

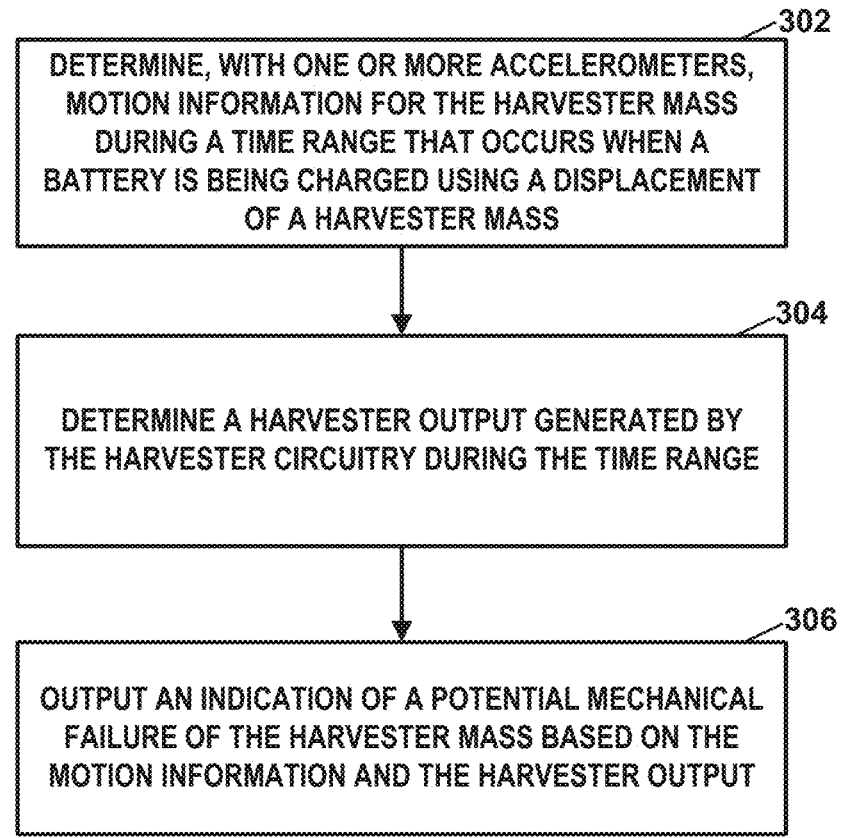

302

DETERMINE, WITH ONE OR MORE ACCELEROMETERS, MOTION INFORMATION FOR THE HARVESTER MASS DURING A TIME RANGE THAT OCCURS WHEN A BATTERY IS BEING CHARGED USING A DISPLACEMENT OF A HARVESTER MASS

304

DETERMINE A HARVESTER OUTPUT GENERATED BY THE HARVESTER CIRCUITRY DURING THE TIME RANGE

306

OUTPUT AN INDICATION OF A POTENTIAL MECHANICAL FAILURE OF THE HARVESTER MASS BASED ON THE MOTION INFORMATION AND THE HARVESTER OUTPUT

FIG. 8

ENERGY HARVESTING SYSTEM INTEGRITY MONITORING

FIELD

This application claims the benefit of U.S. Provisional Patent Application Ser. No. 63/267,202, filed Jan. 27, 2022, the entire content of which is incorporated herein by reference.

This disclosure generally relates to medical devices and, more particularly, to techniques and devices for energy harvesting.

BACKGROUND

Implantable medical devices (IMDs) may sense and monitor electrocardiogram (ECG) signals and other physiological signals, and detect acute health events such as episodes of arrhythmia, cardiac arrest, bradycardia, myocardial infarction, stroke, and seizure. Some IMDs may deliver therapy, e.g., based on monitored physiological signals. Example IMDs include pacemakers and implantable cardioverter-defibrillators, which may be coupled to intravascular or extravascular leads, as well as pacemakers with housings configured for implantation within the heart.

SUMMARY

Some implantable medical devices (IMDs) may include an energy harvesting system that charges a battery of the IMD using a displacement of a harvester mass caused by motion, e.g., heart wall motion and blood flow forces in the case of an intracardiac IMD. However, an energy harvester mechanism implanted in the human heart is subjected to hundreds of millions of repeated mechanical stress cycles over time. Nominally there would be on the order of 40 million heartbeats in one year. An energy harvester would be designed with these conditions in mind. However, due to size constraints, performance constraints, and patient variability, the risk of harvester mechanical permanent deformation, fatigue cracking, or fatigue fracture may still be possible.

Techniques described herein may configure the energy harvesting system to detect a condition of damage (e.g., mechanical and/or electrical) of the harvester mechanism, for example, within a leadless pacemaker, which may help to allow an informed action to be taken to intervene before a battery of the IMD is depleted. For example, the harvesting circuitry may differentiate between a reduction in harvester output due to physiologic changes (e.g., the displacement of a harvester mass caused by motion of the heart) and a reduction in harvester output due to a problem of the harvester mechanism (e.g., harvester circuitry, a harvester mass, piezoelectric beams, or other components of the harvester mechanism).

Techniques described herein may help to provide assurance that an energy harvesting system is operating normally. If there is a change, the system may provide a notification and/or information to a physician and/or patient to differentially diagnose the appropriate action. According to techniques of this disclosure, a system may include harvester circuitry configured to charge a battery of a medical device using a displacement of a harvester mass and one or more accelerometers configured to detect the motion of the implantable medical device. The system is configured to determine motion information (e.g., a number of acceleration counts) and a harvester output (e.g., power or energy)

generated by the harvester circuitry. In this example, the system may output an indication of a potential failure of the harvester mechanism based on the motion information and the harvester output. For instance, the system may output a flag to a physician's device that a harvester mechanism may have a potential failure. Using motion information for a patient may help to improve an accuracy of identification of a failure of the harvester mechanism, which may help to improve a therapy provided to the patient and/or improve an operation of a medical device.

In one example, a system includes harvester circuitry configured to charge a battery for a medical device using a displacement of a harvester mass, one or more accelerometers configured to detect a motion associated with the harvester mass, and processing circuitry. The processing circuitry is configured to determine, with the one or more accelerometers, motion information for the implanted medical device during a time range that occurs when the harvester circuitry charges the battery using the displacement of the harvester mass and determine a harvester output generated by the harvester circuitry during the time range. The processing circuitry is further configured to output an indication of a potential failure of the harvester mechanism based on the motion information and the harvester output.

In another example, a method includes determining, by processing circuitry and with one or more accelerometers, motion information for an implanted medical device during a time range that occurs when harvester circuitry charges a battery using a displacement of the harvester mass and determining, by the processing circuitry, a harvester output generated by the harvester circuitry during the time range. The method further includes outputting, by the processing circuitry, an indication of a potential failure of the harvester mechanism based on the motion information and the harvester output.

In one example, a medical device includes harvester circuitry configured to charge a battery for the medical device using a displacement of a harvester mass, one or more accelerometers configured to detect a motion of the medical device, telemetry circuitry configured for communication, and processing circuitry. The processing circuitry is configured to determine, with the one or more accelerometers, motion information for the implanted medical device during a time range that occurs when the harvester circuitry charges the battery using the displacement of the harvester mass, determine a harvester output generated by the harvester circuitry during the time range, and output an indication of a potential failure of the harvester mechanism based on the motion information and the harvester output.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

FIG. 8 is a flow diagram illustrating an example operation of outputting an indication of a potential failure of a harvester mechanism in accordance with the techniques of the disclosure.

Like reference characters refer to like elements throughout the figures and description.

DETAILED DESCRIPTION

Figure 1:
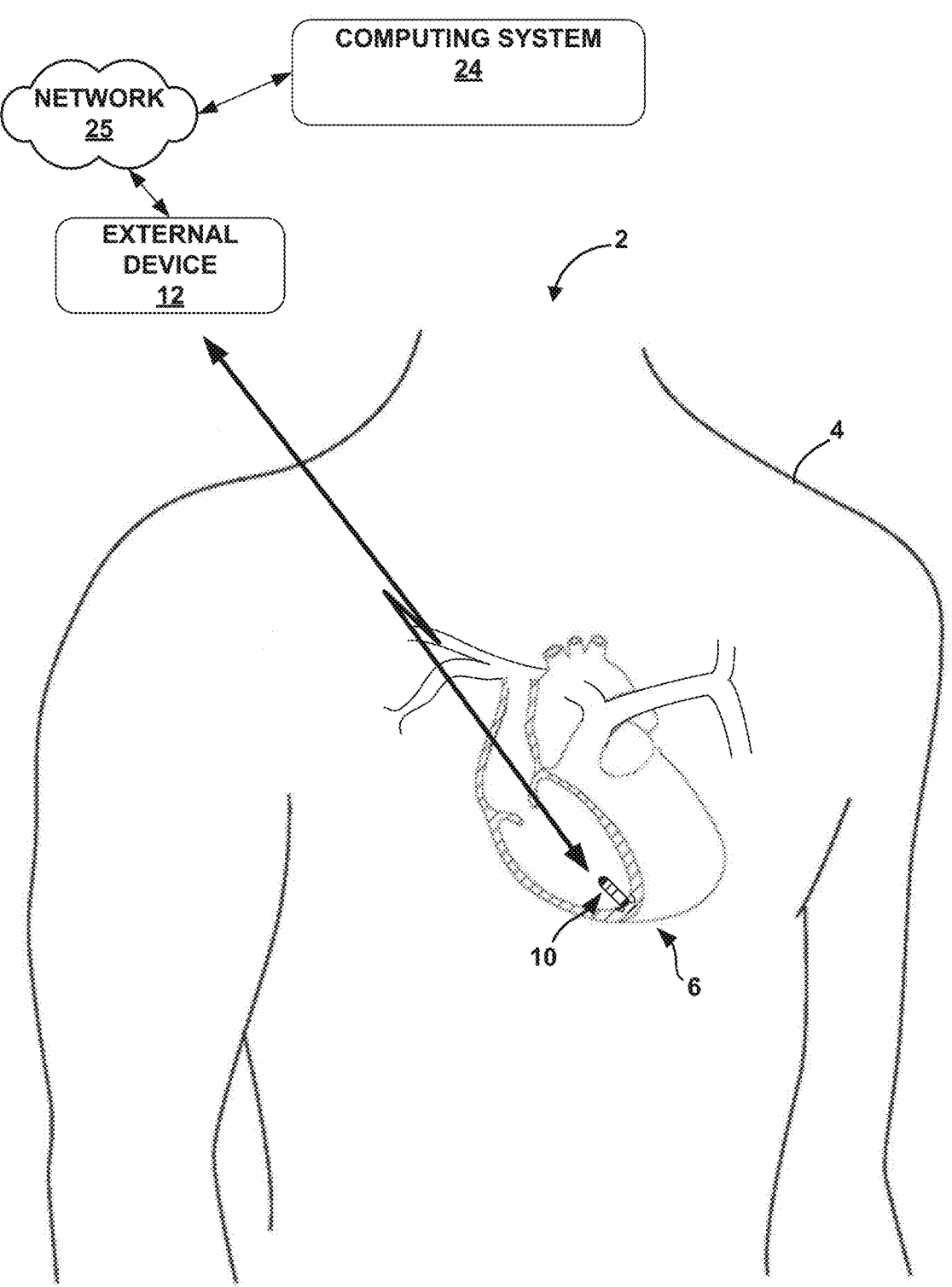
FIG. 1 is a conceptual drawing illustrating an example of a medical device system configured to determine a potential failure of a harvester mechanism using motion information in accordance with the techniques of the disclosure.

An energy harvester implanted in the human heart is subjected to hundreds of millions of repeated mechanical stress cycles over time. Nominally there would be on the order of 40 million heartbeats in one year. An energy harvester would be designed with these conditions in mind. However, due to size constraints, performance constraints, and patient variability, the risk of harvester mechanical permanent deformation, fatigue cracking, or fatigue fracture may still be possible. Techniques described here relate to device health diagnostic sensing for, for example, leadless pacing devices for treatment of bradycardia. However, techniques described herein may be applicable to other device and other treatments of a patient as described further below.

A baseline element of harvester monitoring may be a power monitor over time. However, a change in harvester power output could result from different factors that affect the available energy. For example, the available energy could change due to: (1) a shift in heart rate due to physiologic factors, (2) changes in typical daily posture, (3) a change in the attachment interface between the device and the heart, (4) device encapsulation over implant duration, and/or (5) periods of Afib or AV-block. Without information in addition to power output, if there were a harvester problem (e.g., a mechanical and/or electrical harvester problem), a system may not distinguish the harvester problem from these other causes. Therefore, little guidance may be available to for the system to determine whether any action on the implanted device should be taken.

Descriptions described herein are directed to a use of accelerometers, which may be compact MEMS sensors and/or may have a relatively low power demand. While example described herein use 3-axis accelerometer signals, other signals may be used to determine a failure in the harvester mechanism. For example, a harvester mechanism may additionally, or alternatively, use one or more of a 3-axis gyroscope, a 3-axis magnetometer, a 3-axis force sensors, or a torque sensor to determine a failure in the harvester mechanism. In some examples, the harvester mechanism may use temperature to determine a failure in the harvester mechanism. The harvester mechanism may use a cardiac electrical signal (e.g. an electrogram or "EGM") to determine a failure in the harvester mechanism, which may give an indication of the nature of the heart contracting. Techniques described herein for determining a failure in the harvester mechanism may use combinations of signals. For example, the harvester mechanism may use one or more of accelerometer signals, a 3-axis gyroscope, a 3-axis magnetometer, a 3-axis force sensors, a torque sensor, a temperature, or a cardiac signal to determine a failure in the harvester mechanism.

Techniques described herein provide a system configured to detect a condition of potential damage of a harvester mechanism incorporated within a medical device (e.g., a leadless pacemaker). In this way, the system may inform a physician, caretaker, patient or another person of action to be taken to intervene before a battery of the medical device is depleted. Moreover, techniques described herein may account for motion information (e.g., a number of acceleration counts), which may help to differentiate between a reduction in the harvester output due to physiologic changes (e.g., reflected in a change in the motion information) and a reduction in harvester output due to a harvester problem. Accordingly, techniques described herein may help to provide assurance that an energy harvesting system is operating normally. If there is a change in the energy harvesting system, the system may provide a notification and information to the physician, caretaker, patient, or other person to differentially diagnose the appropriate action.

For example, the system may provide a differential diagnostic of an integrity of an implanted energy harvester. For example, the system may distinguish between a decrease in energy output by the energy harvester due to physiologic changes of the patient and a decrease in energy output by the energy harvester due to a failure of the harvester mechanism. The system may store a trend of an energy generated by a displacement of the harvester mass and the motion information (e.g., a number of acceleration counts). The energy generated by a displacement of the harvester mass may refer to an integrated sum of power output by the energy harvester over a set period of time, for example 1 minute. The motion information may include a sum of all 3 accelerometer axis directions measured over a fixed time period, for example 1 minute. In some examples, the motion information may include a number of acceleration counts. The number of acceleration counts may include number of cardiac counts. Cardiac counts may indicate the sum of all 3 accelerometer axis directions filtered in the cardiac motion band (e.g., approximately 10 Hz-30 Hz). The number of acceleration counts may include a number of harvester counts. Harvester counts may refer to the sum of all 3 accelerometer axis directions filtered by a bandpass filter centered around the harvester resonance frequency with a tolerance (e.g., +/−10%). In some examples, the number of acceleration counts may include a single vector. The single accelerometer vector may be selected in accordance with the preferred harvester output direction (e.g., a direction of motion of the harvester mass for charging). In some examples, the single vector may be a virtual vector derived from two or more of the physical accelerometer axes.

Moreover, techniques described herein may report out trend information through wireless monitoring. For example, a system may identify a slope of a curve fit function (e.g., linear regression) corresponding to energy generated per acceleration count. The system may trigger a notification to the patient that there is a trend metric (e.g., decreasing power output for constant motion information) that merits attention by their physician. In this way, techniques described herein using motion information (e.g., a number of acceleration counts) may help to provide information to users, such as physicians and patients, about the safety of an implanted energy harvesting system, which may help to improve adoption of the system by assuring such users that there are fail-safe monitors incorporated into the system. Moreover, techniques described herein using motion information (e.g., a number of acceleration counts) may help to reduce the cost of lesser harvesting system build quality, by decreasing the probability of hazard and harm if there were a problem with the operation of the system.

In some examples, the system may improve the accuracy of detecting a potential failure in the harvester mechanism by accounting for patient posture. For example, the system may determine a potential failure in the harvester mechanism based on a posture vector. A posture vector may refer to an accelerometer 3-axis output after a low-pass filter that removes the cardiac signals, which may improve the accuracy in detecting a potential failure of the harvester mechanism, for example, by tuning a reporting of motion information to the design characteristics of the harvester mechanism. The posture vector may help to define the orientation of the harvester mass device with respect to gravity.

FIG. 1 is a conceptual drawing illustrating an example of a medical device system 2 configured to determine a potential failure of a harvester mechanism using motion information in accordance with the techniques of the disclosure. The example techniques may be used with an IMD 10, which may be in wireless communication with an external device 12. The techniques of this disclosure will be explained using an implantable intracardiac pacemaker device, but the described techniques are not limited to such a device. The techniques may, for example, also be implemented in other types of implantable medical devices, such as defibrillation devices, neurostimulation devices, and drug pumps, as well as insertable and wearable devices.

In the example of FIG. 1, IMD 10 is implanted with heart 6 of patient 4 (e.g., in the right ventricular location illustrated in FIG. 1). In other examples, IMD 10 may be implanted within other chambers of the heart, on the heart, or at other locations within patient 4. IMD 10 includes at least one accelerometer and a plurality of electrodes (not shown in FIG. 1) and is configured to sense a cardiac EGM. IMD 10 may also include additional sensors, such as optical and impedance sensors. In some examples, IMD 10 takes the form of the MICRA™ Transcatheter Pacing System, available from Medtronic, Inc. The techniques of this disclosure may be implemented in systems including any one or more implantable or external medical devices, including monitors, pacemakers, or defibrillators.

External device 12 is a computing device configured for wireless communication with IMD 10. External device 12 may be configured to communicate with computing system 24 via network 25. In some examples, external device 12 may provide a user interface and allow a user to interact with IMD 10. Computing system 24 may comprise computing devices configured to allow a user to interact with IMD 10, e.g., data collected from IMD or programmable parameters of IMD 10, via network 25.

In some examples, computing system 24 includes one or more handheld computing devices, computer workstations, servers or other networked computing devices. A device of computing system 24 may represent a physician's device. In some examples, computing system 24 may include one or more devices, including processing circuitry and storage devices. Computing system 24 and network 25 may be implemented, fully or partially, by the Medtronic Carelink™ Network or other patient monitoring systems.

Network 25 may include one or more computing devices (not shown), such as one or more non-edge switches, routers, hubs, gateways, security devices such as firewalls, intrusion detection, and/or intrusion prevention devices, servers, computer terminals, laptops, printers, databases, wireless mobile devices such as cellular phones or personal digital assistants, wireless access points, bridges, cable modems, application accelerators, or other network devices. Network 25 may include one or more networks administered by service providers, and may thus form part of a large-scale public network infrastructure, e.g., the Internet. Network 25 may provide computing devices, such as computing system 24 and IMD 10, access to the Internet, and may provide a communication framework that allows the computing devices to communicate with one another. In some examples, network 25 may be a private network that provides a communication framework that allows computing system 24, IMD 10, and/or external device 12 to communicate with one another but isolates one or more of computing system 24, IMD 10, or external device 12 from devices external to network 25 for security purposes. In some examples, the communications between computing system 24, IMD 10, and external device 12 are encrypted.

In accordance with the techniques of the disclosure, IMD 10 may determine, with the one or more accelerometers, motion information for a harvester mass of IMD 10 during a time range that occurs when harvester circuitry charges a battery of IMD 10 using a displacement of the harvester mass by heart 6. For example, IMD 10 may determine a number of acceleration counts for a period of time (e.g., a 1 minute period of time). IMD 10 may determine a harvester output (e.g., power, voltage, current, or energy) generated using the displacement of the harvester mass during the time range that occurs when the harvester circuitry charges the battery using the displacement of the harvester mass. For example, IMD 10 may determine a power generated by the harvester system (e.g., the harvester mass and the harvester circuitry) during the period of time (e.g., a 1 minute period of time) for the number of acceleration counts. In this example, IMD 10 may output an indication of a potential failure of the harvester mechanism based on the motion information and the power generated. For example, IMD 10 may output the indication of the potential failure of the harvester mechanism when a ratio (e.g., the power generated by the harvester system divided by the number of acceleration counts) is less than a notification threshold. In some examples, IMD 10 may output the indication of the potential failure of the harvester mechanism when a trend metric indicates that power generated by a current set of metrics for IMD 10 is less than power generated by a previous set of metrics for IMD 10 by at least a threshold value.

Figure 2:
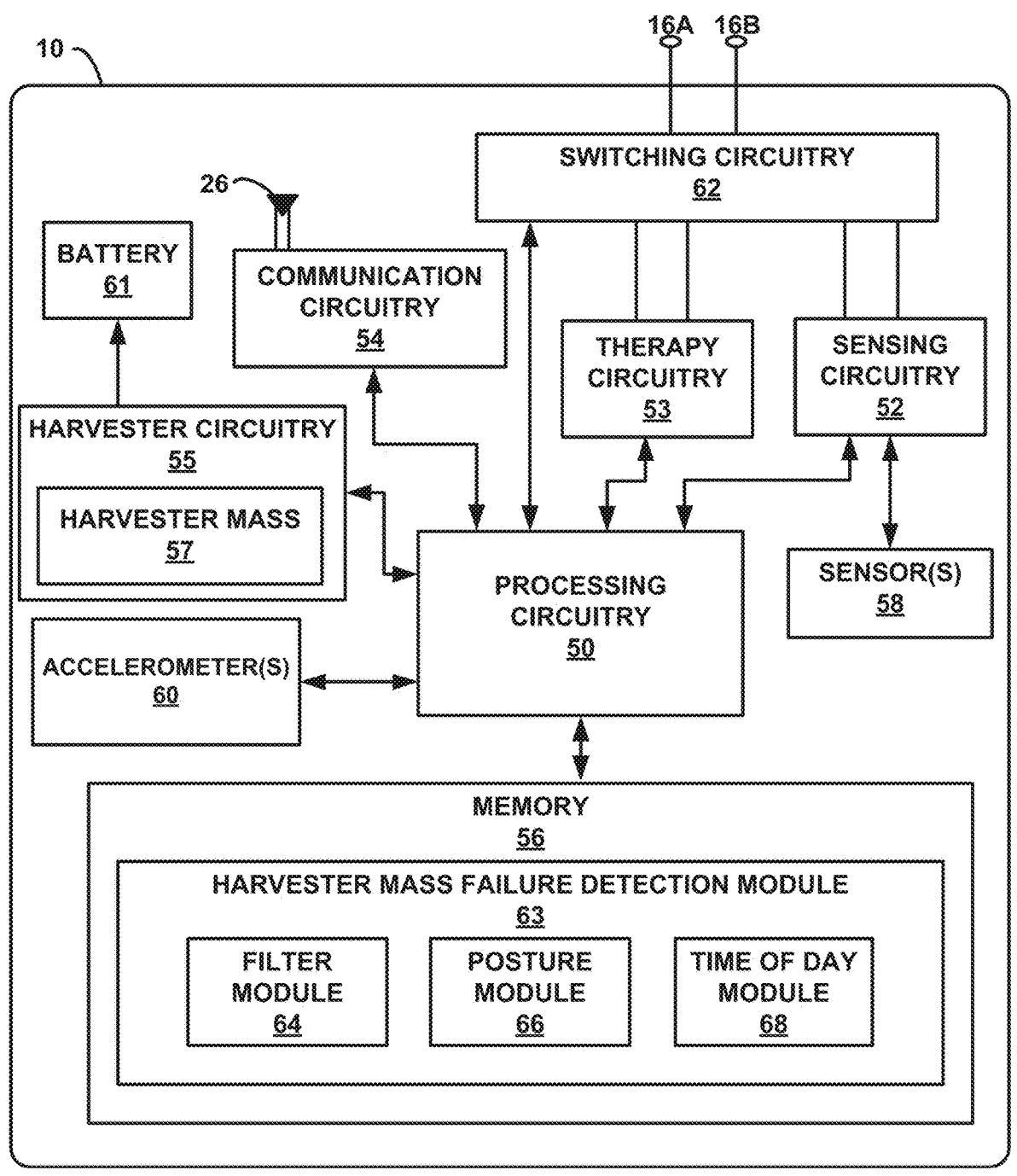
FIG. 2 is a block diagram illustrating an example configuration of the implantable medical device (IMD) of FIG. 1.

FIG. 2 is a block diagram illustrating an example configuration of IMD 10 of FIG. 1. As shown in FIG. 2, IMD 10 includes processing circuitry 50, sensing circuitry 52, therapy circuitry 53, communication circuitry 54, harvester circuitry 55, memory 56, sensors 58, accelerometers 60, battery 61, switching circuitry 62, and electrodes 16A, 16B (hereinafter "electrodes 16"), one or more of which may be disposed on a housing of IMD 10. In some examples, memory 56 includes computer-readable instructions that, when executed by processing circuitry 50, cause IMD 10 and processing circuitry 50 to perform various functions attributed herein to IMD 10 and processing circuitry 50. Memory 56 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 may be selectively coupled to electrodes 16A, 16B via switching circuitry 62 as controlled by processing circuitry 50. Sensing circuitry 52 may monitor signals from electrodes 16A, 16B in order to monitor electrical activity of heart 6 of patient 4 of FIG. 1 and produce cardiac EGM data for patient 4. In some examples, processing circuitry 50 transmits, via communication circuitry 54, one or more of motion information, harvester output, or an indication of a potential failure of a harvester mechanism of IMD 10, for patient 4 to an external device, such as external device 12 of FIG. 1.

In some examples, IMD 10 includes one or more sensors 58, such as one or more optical sensors, impedance sensors, microphones, and/or pressure sensors. Sensors 58 may also include one or more of additional sensors configured to be controlled based on detected movement, continuously-running sensors, or sensors controlled based on factors other than detected movement.

In some examples, sensing circuitry 52 may include one or more filters and amplifiers for filtering and amplifying signals received from one or more of electrodes 16A, 16B and/or other sensors 58. In some examples, sensing circuitry 52 and/or processing circuitry 50 may include a rectifier, filter and/or amplifier, a sense amplifier, comparator, and/or analog-to-digital converter.

Therapy circuitry 53 may be selectively coupled to electrodes 16A, 16B via switching circuitry 62 as controlled by processing circuitry 50. Therapy circuitry 53 is configured to generate and deliver electrical therapy to heart 6. Therapy circuitry 53 may include one or more pulse generators, capacitors, and/or other components capable of generating and/or storing energy to deliver as electrical therapy, e.g., pacing therapy or other tissue stimulating therapy. Delivery of therapy by therapy circuitry 53 may be controlled by processing circuitry 50 based on signals sensed by sensing circuitry 52.

Harvester circuitry 55 may be configured to charge battery 61 using a displacement of harvester mass 57. Harvester mass 57 may comprise a piezoelectric transducer. For example, harvester mass 57 may be configured to be displaced by a motion from heart 6 of patient 4 and/or blood flow resulting from the motion from heart 6. For instance, IMD 10 may be attached to a wall of heart 6. In this example, harvester circuitry 55 may be configured to generate, using the displacement, electrical current for charging battery 61.

Harvester mechanism failure detection module 63 (also referred to herein as simply "detection module 63") may be configured to, when executed by processing circuitry 50, determine whether a potential failure of harvester mechanism has occurred. For example, processing circuitry 50 may record and trend a ratio value (e.g., an energy transfer ratio). Processing circuitry 50 may establish a baseline value for the ratio value. For example, processing circuitry 50 may collect a first baseline daily data at a time of implant of IMD 10 with patient 4 is in a supine position. Harvester output may represent a measure of power (e.g. micro-watts). Motion information may represent a number of accelerometer counts (e.g., an integrated sum over time). A posture vector may include a number of accelerometer counts.

While examples herein may refer to motion information as representing a number of accelerometer counts, detection module 63 may additionally, or alternatively, use other motion information to detect a failure in the harvester mechanism. For example, detection module 63 may use motion information that represents one or more of a maximum over the cardiac cycle or the mean or median over the cardiac cycle to detect a failure in the harvester mechanism. In some examples, detection module 63 may use motion information that represents a filtered set of values for one or more of a count, a maximum over the cardiac cycle, or the mean or median over the cardiac cycle to detect a failure in the harvester mechanism. As used herein "counts" may refer to the an integrated sum over time. In some examples, "counts" may refer to an instantaneous count such as, for example, a reading from a sensor.

Processing circuitry 50 may compute a ratio value as the ratio of the harvester output to the available acceleration. For example, processing circuitry 50 may determine an energy transfer ratio for a time range based on the harvester output generated by harvester circuitry 55 during the time range and motion information for harvester mass 57. For instance, processing circuitry 50 may determine an energy transfer ratio by dividing the power generated by harvester circuitry 55 during the time range by a number of acceleration counts for harvester mass 57. In this example, processing circuitry 50 may output an indication of a potential failure of the harvester mechanism (e.g., harvester mass 57) in response to a determination that the energy transfer ratio satisfies a threshold value. In some examples, processing circuitry 50 may determine the threshold value based on the baseline value (e.g., a percentage of the baseline value).

Processing circuitry 50 may define a threshold at which a notification for investigation should be triggered. For example, processing circuitry 50 may set a baseline trigger setting to a transfer ratio at 50% of the baseline value. Also, a trigger setting on a reduction of available acceleration from baseline could be defined, for example, a reduction of available acceleration at 50% of the baseline value.

In some examples, processing circuitry 50 may determine a trend metric. For example, processing circuitry 50 may determine a current set of metrics based on the energy and the number of acceleration counts. In this example, processing circuitry 50 may compare the current set of metrics with a previous set of metrics to generate a trend metric. For instance, processing circuitry 50 may determine a first polynomial expression based on the previous set of metrics (e.g., apply a linear regression on pairs of power and accelerometer counts of the previous set of metrics). In this instance, processing circuitry 50 may determine a second polynomial expression based on the current set of metrics (e.g., apply a linear regression on pairs of power and accelerometer counts of the current set of metrics). Processing circuitry 50 may compare the current set of metrics with the previous set of metrics. For example, in response to a determination that the second polynomial expression indicates a smaller slope than the first polynomial expression by at least a threshold value, processing circuitry 50 may determine that the potential failure has occurred at the harvester mechanism (e.g., harvester mass 57).

Processing circuitry 50 may monitor the harvester output power from harvester circuitry 55 and motion information (e.g., available acceleration) over time. For example, processing circuitry 50 may record and store the daily data at the rate of 1 reading per day for the last 15 days, and then the min/max per week for the last 80 weeks.

Processing circuitry 50 may, at the time of remote monitoring (e.g., CareLink®) provide an uplink of the trend data. If the latest trend ratio is below the notification threshold, or the trend ratio has been below the latest notification threshold since the last wireless transmission, processing circuitry 50 may flag the condition in the CareLink® summary report to "Investigate Energy Harvester Performance." If there is a trend of lower available acceleration, and the ratio value of accelerometer to harvester is constant, that may indicate a physiologic change. If the available acceleration is below the threshold, processing circuitry 50 may flag the condition in the CareLink® summary report to "Investigate Reduction in Available Energy from Cardiac Contraction."

Posture module 66, when executed by processing circuitry 50, may account for a posture of patient 4. For example, patient posture may affect the available accelerations and harvester output. For example, processing circuitry 50 may record a posture vector as part of the baseline data collection and as part of the daily data. Processing circuitry 50 may combine all readings from accelerometers 60 and/or from harvester circuitry 55 (e.g., a power during a time range) together in generating trends, as if posture was not a factor. This may be sufficiently effective due to reporting medians and trends over time.

Posture module 66, when executed by processing circuitry 50, may report the trend results over time segregated by posture bins of into different postures (e.g., supine, left-lateral, right-lateral, or prone). Over time processing circuitry 50 may determine a most common sleeping position posture and the data reporting and monitoring could be refined to show only the determined posture that is most common and for which there is the most data. Posture module 66, when executed by processing circuitry 50, may restrict the monitoring data to only those conditions that match the baseline data posture condition, e.g., the supine posture. This approach would work well for patients that typically sleep in the supine position.

Posture module 66, when executed by processing circuitry 50, may capture additional trend data with day-time readings, when patient 4 is likely to be upright. This may be the primary time over which harvester circuitry 55 may provide energy to battery 61. By storing the posture vector, randomly collected samples of daily data, could be used to determine whether patient 4 is in an upright posture or not in the upright position.

Filter module 64, when executed by processing circuitry 50, may improve the accuracy of detection module 63 by tuning the reporting of the motion information to the mechanical design characteristics of harvester mass 57. For example, processing circuitry 50 may report motion information in terms of the typical cardiac signal frequencies, e.g. nominally 10 Hz to 30 Hz.

In some examples, filter module 64, when executed by processing circuitry 50, may filter for a specific energy harvester design of harvester mass 57. For example, processing circuitry 50 may be set to filter based on a specific first natural frequency at which harvester mass 57 provides the most energy. In this example, processing circuitry 50 may apply a specific narrow bandpass filter designed to be centered around the natural frequency of harvester mass 57. For example, if the natural frequency of harvester mass 57 were 20 Hz, a bandpass filter could be designed to accept signals between 18 Hz and 22 Hz. This may make the relationship between the harvester output and the available accelerations even more accurate.

Time of day module 68, when executed by processing circuitry 50, may filter for a daily data. For example, processing circuitry 50 may measure available acceleration, a posture vector, and an energy harvester output for a particular time of day (e.g., daytime or nighttime). In some examples, processing circuitry 50 may determine nighttime repeated measurements at a median of 5 measurements every 30 minutes between 1 AM and 3 AM. In some examples, processing circuitry 50 may further determine hourly measurements during the day-time.

Figure 3:
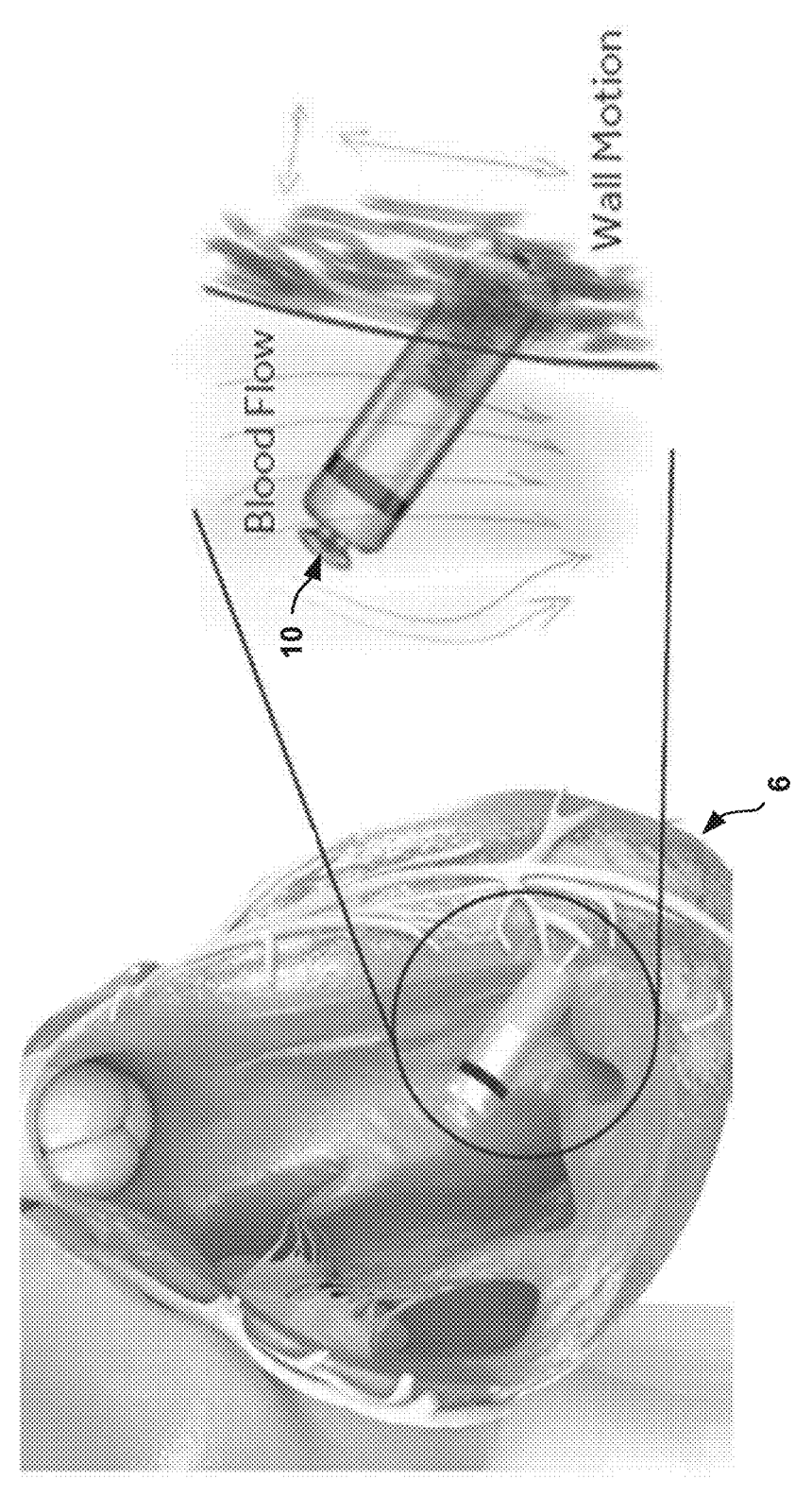
FIG. 3 shows a conceptual drawing of an example medical device for energy harvesting in accordance with the techniques of the disclosure.

FIG. 3 shows a conceptual drawing of an example medical device 10 for energy harvesting in accordance with the techniques of the disclosure. Heart wall motion of heart 6 and blood flow may generate forces that displace IMD 10, which may represent an implanted leadless pacemaker. The displacement of IMD 10 may displace a harvester mass 57 of IMD 10 and displaces proof masses in one or more accelerometers of IMD 10, resulting in motion information (e.g., accelerometer signals). In accordance with the techniques of the disclosure, IMD 10 may record, monitor, and report temporal trends in harvester output and motion information to provide a differential diagnostic of the integrity of an energy harvesting system (e.g., harvester circuitry) of IMD 10.

Figure 4A:
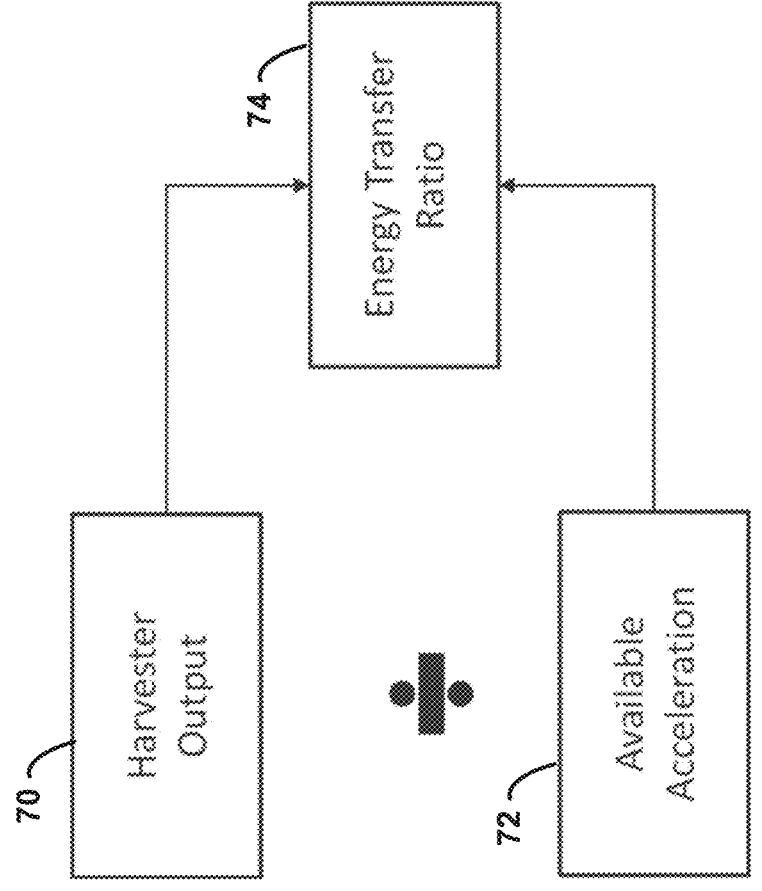
FIG. 4A shows a conceptual drawing of an energy transfer ratio in accordance with the techniques of the disclosure.

FIG. 4A shows a conceptual drawing of an energy transfer ratio in accordance with the techniques of the disclosure. In the example of FIG. 4A, IMD 10 (e.g., harvester circuitry 55) may generate a harvester output 70. The harvester output may represent a power generated using the displacement of harvester mass 57 during the time range that occurs when harvester circuitry 55 charges battery 61 using the displacement of harvester mass 57. For instance, one or more of actual power, current, or voltage (e.g., a sum or averages for time period) may represent a harvester output. IMD 10 (e.g., accelerometers 60) may generate available acceleration 72. Available acceleration 72 may represent a number of acceleration counts for harvester mass 57 during the time range that occurs when harvester circuitry 55 charges battery 61 using the displacement of harvester mass 57. As used herein, a number of acceleration counts may refer to one or more of a number of counts of threshold crossings and/or integration/sum of the signal for time periods. The number of acceleration counts may include any value/quantification representing an amount of acceleration for a time period. IMD 10 (e.g., processing circuitry 50) may determine an energy transfer ratio 74 based on the harvester output 70 and the available acceleration 72. For example, IMD 10 may divide harvester output 70 by available acceleration 72 to generate energy transfer ratio 74.

Figures 4B, 4C:
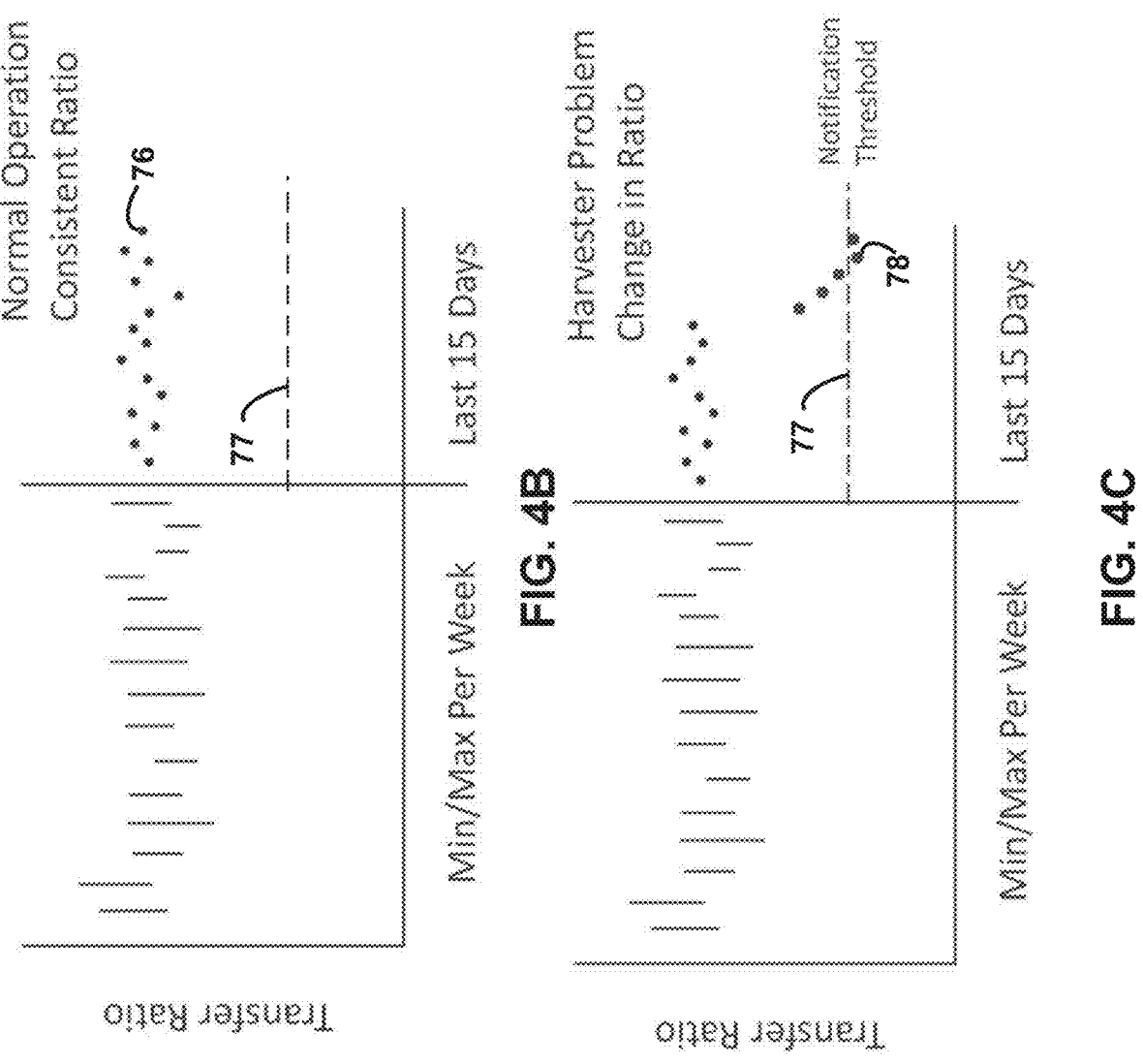
FIG. 4B shows a chart of an energy transfer ratio that does not satisfy a notification threshold in accordance with the techniques of the disclosure.
FIG. 4C shows a chart of an energy transfer ratio that satisfies a notification threshold in accordance with the techniques of the disclosure.

FIG. 4B shows a chart of an energy transfer ratio that does not satisfy a notification threshold 77 in accordance with the techniques of the disclosure. In FIG. 4B, the abscissa axis represents time and the ordinate axis represents the energy transfer ratio. In the example of FIG. 4B, energy transfer ratio 76 does not satisfy (e.g., is greater than) notification threshold 77. As such, IMD 10 may refrain from outputting an indication of a potential failure of the harvester mechanism (e.g., harvester mass 57).

FIG. 4C shows a chart of an energy transfer ratio that satisfies notification threshold 77 in accordance with the techniques of the disclosure. In FIG. 4C, the abscissa axis represents time and the ordinate axis represents the energy transfer ratio. In the example of FIG. 4C, energy transfer ratio 78 satisfies (e.g., is less than) notification threshold 77. As such, IMD 10 may output an indication of a potential failure of the harvester mechanism (e.g., harvester mass 57).

In the example of FIG. 4C, IMD 10 may output an indication of a potential failure of the harvester mechanism in response to only one output of a daily measure of the transfer ratio 78 falling below notification threshold 77. In some examples, however, IMD 10 may output an indication of a potential failure of the harvester mechanism in response to at least X number of the last Y outputs of the transfer ratio 78 falling below notification threshold 77, where X and Y are positive integers and where X is less than Y. For instance, IMD 10 may output an indication of a potential failure of the harvester mechanism in response to at least 4 of the last 7 of the transfer ratio 78 falling below notification threshold 77. A user may set notification threshold 77 relatively high and configure IMD 10 to output the indication of a potential failure of the harvester mechanism in response to at least X number of the last Y outputs of the transfer ratio 78 falling below notification threshold 77. In some examples, the user may set notification threshold 77 relatively low and configure IMD 10 may output the indication of a potential failure of the harvester mechanism in response to only one output of transfer ratio 78 falling below notification threshold 77.

Notification threshold 77 may represent a static level set by the user or auto-established by IMD 10 (e.g., after one week of operation). For example, notification threshold 77 may be set at 50% of a baseline value, at 33% of the base line value, or set to 75% of the baseline value. However, IMD 10 may dynamically auto-adjust over time.

Figures 5A, 5B, 5C, 5D:
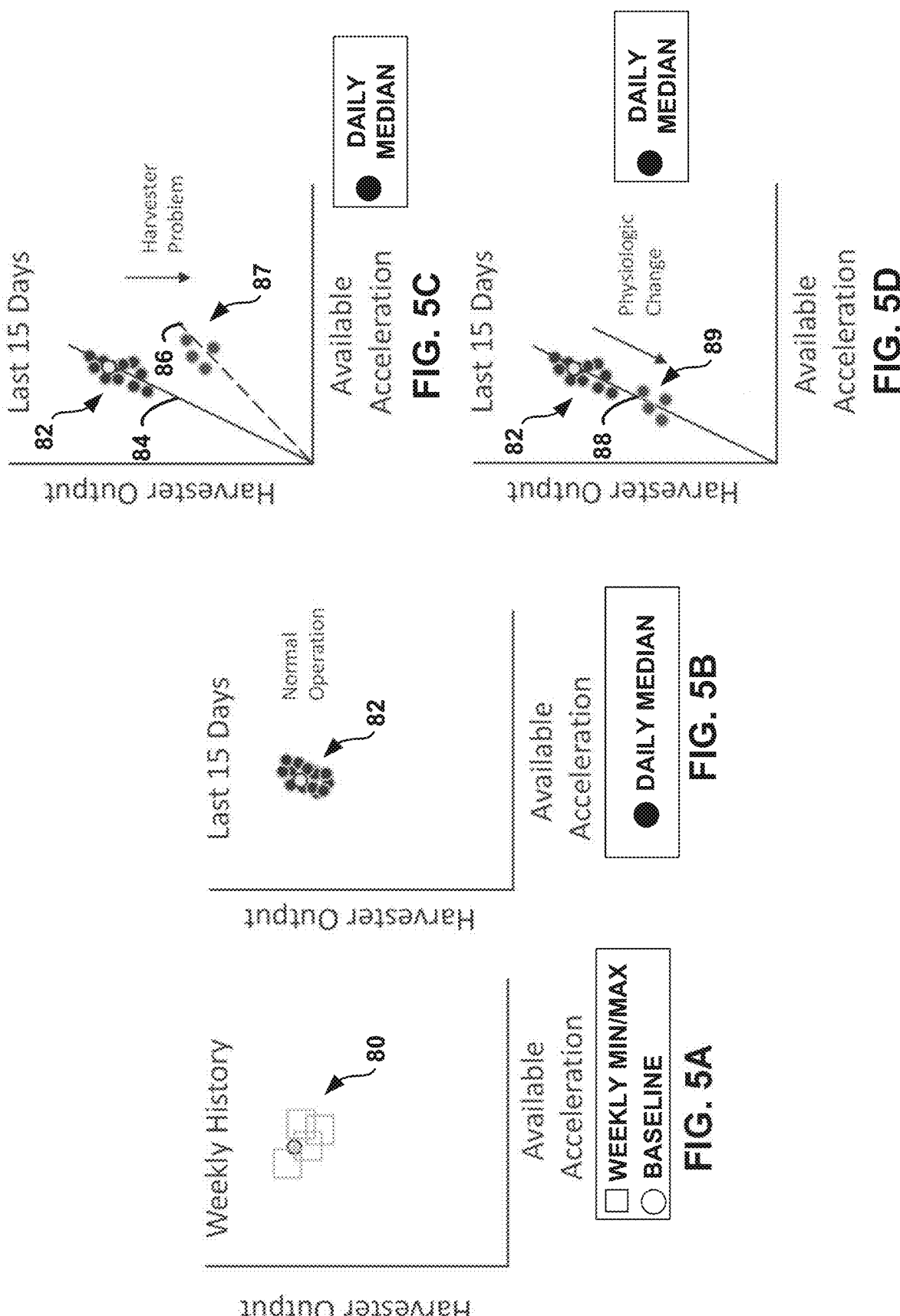
FIG. 5A shows a chart of a baseline of an energy transfer ratio for a weekly history in accordance with the techniques of the disclosure.
FIG. 5B shows a chart of a baseline of an energy transfer ratio for a 15 day history in accordance with the techniques of the disclosure.
FIG. 5C shows a chart of a harvester mass that has a potential failure in accordance with the techniques of the disclosure.
FIG. 5D shows a chart of a harvester mass that does not have a potential failure in accordance with the techniques of the disclosure.

FIG. 5A shows a chart of a baseline of an energy transfer ratio for a weekly history in accordance with the techniques of the disclosure. In FIG. 5A, the abscissa axis represents available acceleration (e.g., a number of acceleration counts) and the ordinate axis represents the harvester output (e.g., power generated by harvester circuitry 55). In the example of FIG. 5A, IMD 10 or another device of system 2 may determine a baseline value from weekly min/max ranges 80.

FIG. 5B shows a chart of a baseline of an energy transfer ratio for a 15 day history in accordance with the techniques of the disclosure. In FIG. 5B, the abscissa axis represents available acceleration (e.g., motion information, or more specifically, a number of acceleration counts) and the ordinate axis represents the harvester output (e.g., power generated by harvester circuitry 55). In the example of FIG. 5B, IMD 10 or another device of system 2 may determine a previous set of metrics 82, where each pair of harvester output and the available acceleration represents a daily median value.

FIG. 5C shows a chart of a harvester mass 57 that has a potential failure in accordance with the techniques of the disclosure. In FIG. 5C, the abscissa axis represents available acceleration (e.g., motion information, or more specifically, a number of acceleration counts) and the ordinate axis represents the harvester output (e.g., power generated by harvester circuitry 55). In the example of FIG. 5C, IMD 10 or another device of system 2 may determine a first curve 84 that represents a first polynomial expression based on previous set of metrics 82. For instance, IMD 10 or another device of system 2 may apply linear regression to previous set of metrics 82 to determine first curve 84. In this example, IMD 10 or another device of system 2 may determine a second curve 86 that represents a second polynomial expression based on a current set of metrics 87. For instance, IMD 10 or another device of system 2 may apply linear regression to current set of metrics 87 to determine second curve 86. In response to a determination that the second polynomial expression of second curve 86 indicates a smaller slope than the first polynomial expression of first curve 84 by at least a threshold value, IMD 10 or another device of system 2 may determine that a potential failure has occurred at the harvester mechanism.

IMD 10 may output an indication of a potential failure of the harvester mechanism in response to only one occurrence of the slope of the second polynomial expression of second curve 86 being smaller than the slope of the first polynomial expression of first curve 84 by at least a threshold value. In some examples, however, IMD 10 may output an indication of a potential failure of the harvester mechanism in response to at least X number of the last Y slopes of the second polynomial expression of second curve 86 being smaller than the slope of the first polynomial expression of first curve 84 by at least the threshold value, where X and Y are positive integers and where X is less than Y. For instance, IMD 10 may output an indication of a potential failure of the harvester mechanism in response to at least 4 of the last 7 slopes of the second polynomial expression of second curve 86 being smaller than the slope of the first polynomial expression of first curve 84 by at least the threshold value.

FIG. 5D shows a chart of a harvester mechanism that does not have a potential failure in accordance with the techniques of the disclosure. In FIG. 5D, the abscissa axis represents available acceleration (e.g., motion information, or more specifically, a number of acceleration counts) and the ordinate axis represents the harvester output (e.g., power generated by harvester circuitry 55). In the example of FIG. 5D, IMD 10 or another device of system 2 may determine a curve 89 that represents a first polynomial expression based on previous set of metrics 82. For instance, IMD 10 or another device of system 2 may apply linear regression to previous set of metrics 82 to determine first curve 84. In this example, IMD 10 or another device of system 2 may determine that curve 88 that represents a second polynomial expression based on a current set of metrics 89. For instance, IMD 10 or another device of system 2 may apply linear regression to current set of metrics 89 to determine curve 88. In response to a determination that the second polynomial expression for current set of metrics 89 does not indicate a smaller slope than the first polynomial expression for previous set of metrics 82 by at least a threshold value, IMD 10 or another device of system 2 may determine that a potential failure has not occurred at the harvester mechanism.

Figure 6:
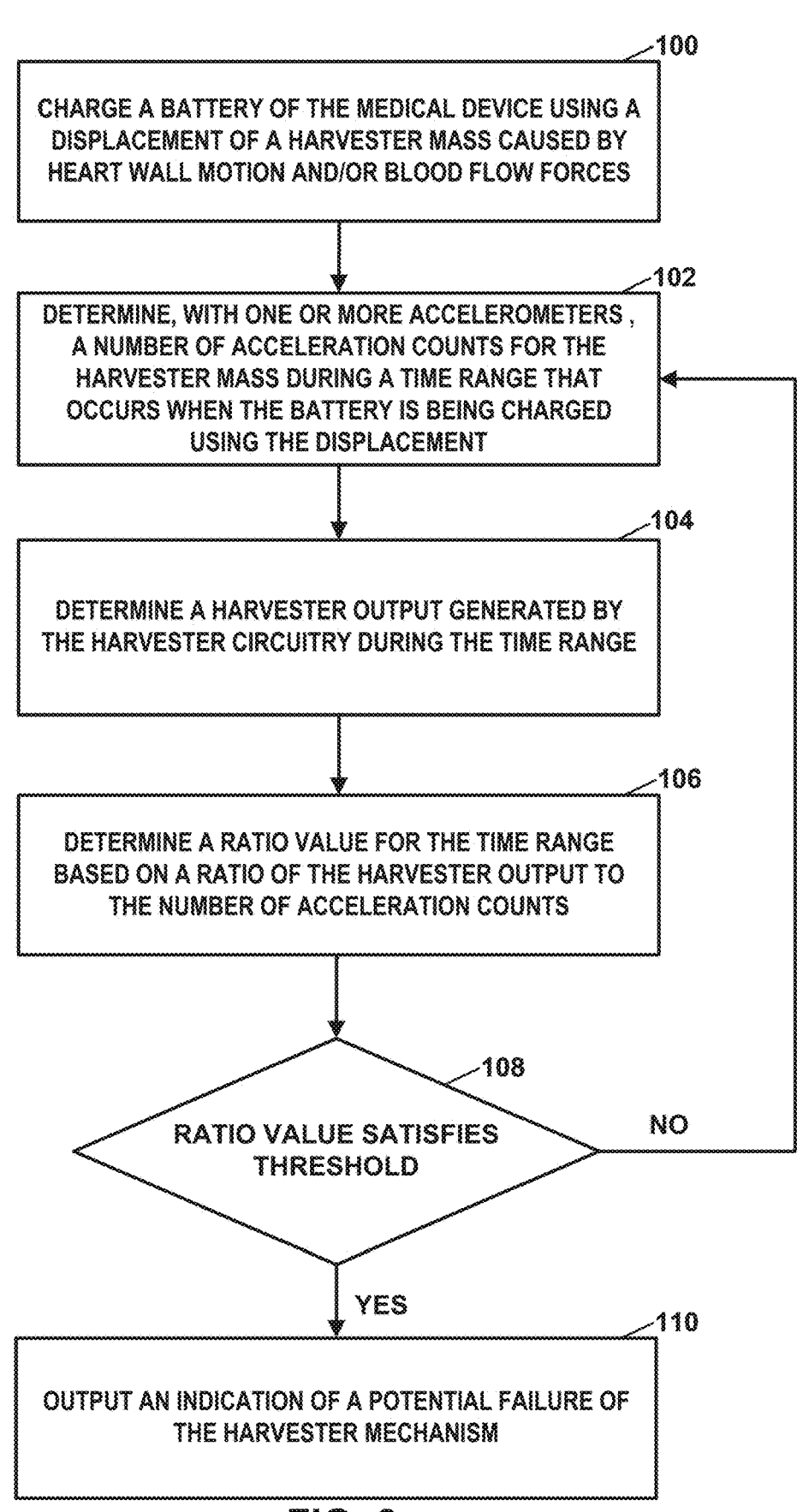
FIG. 6 is a flow diagram illustrating an example operation of determining a ratio value in accordance with the techniques of the disclosure.

FIG. 6 is a flow diagram illustrating an example operation of determining an energy transfer ratio in accordance with the techniques of the disclosure. FIG. 6 is discussed with FIGS. 1-5 for example purposes only. In accordance with the techniques of the disclosure, harvester circuitry 55 may charge battery 61 of medical device 10 using a displacement of harvester mass 57 caused by heart wall motion and/or blood flow forces (100). Processing circuitry 50 may determine, with the one or more accelerometers 60, a number of acceleration counts for harvester mass 57 during a time range that occurs when harvester circuitry 55 charges battery 61 using the displacement of harvester mass 57 (102). Processing circuitry 50 may determine the number of acceleration counts as an integral sum of acceleration of medical device 10 over time.

In some examples, processing circuitry 50 may determine the number of acceleration counts based on posture information for the patient. For instance, processing circuitry 50 may determine the number of acceleration counts to count each acceleration count that is associated with a posture indicated by the posture information for the patient and to refrain from counting acceleration counts that are associated with a posture different from the posture indicated by the posture information for the patient. Processing circuitry 50 may determine the number of acceleration counts based on a time of day. For instance, processing circuitry 50 may determine the number of acceleration counts to count each acceleration count that occurs during a first time range (e.g., night) and to refrain from counting acceleration counts that occur during a second time range (e.g., daytime).

In some examples, processing circuitry 50 may filter an output of one or more accelerometers 60. For example, processing circuitry 50 may filter an output of one or more accelerometers 60 using a band pass filter corresponding to 10 Hz to 30 Hz. In some examples, processing circuitry 50 may filter an output of one or more accelerometers 60 using a natural frequency of harvester mass 57. Processing circuitry 50 may filter an output of one or more accelerometers 60 to comprise a single vector corresponding to a single direction of acceleration of harvester mass 57.

Processing circuitry 50 may determine a harvester output generated by harvester circuitry 55 during the time range (104). The harvester output may include a power generated by harvester circuitry 55 using the displacement of harvester mass 57 during the time range that occurs when harvester circuitry 55 charges the battery using the displacement of harvester mass 57. Processing circuitry 50 may determine the harvester output based on a time of day. For instance, processing circuitry 50 may determine the harvester output to include power generated during a first time range (e.g., night) and to refrain from counting power generated during a second time range (e.g., daytime).

Processing circuitry 50 may determine a ratio value for the time range based on a ratio of the harvester output to the number of acceleration counts (106). For example, processing circuitry 50 may determine the ratio value as the harvester output divided by the number of acceleration counts. Processing circuitry 50 may determine whether the ratio value satisfies a threshold value (108). Processing circuitry 50 may determine the threshold value based on a baseline value. In response to a determination that the ratio value does not satisfy the threshold value ("NO" of step 108), the process returns to step 102.

In response, however, to a determination that the ratio value satisfies the threshold value ("YES" of step 108), processing circuitry 50 may output an indication of a potential failure of the harvester mechanism (110). For example, in response to a determination that the ratio value satisfies a threshold value that is a percentage (e.g., less than 100%, less than 90%, less than 50%, etc.) of the baseline value, processing circuitry 50 may output an instruction to cause external device 12 to output the indication of the potential failure of the harvester mechanism. In some examples, processing circuitry 50 may output an instruction to cause a physician device (e.g., computing system 24) to output the indication of the potential failure of the harvester mechanism. Processing circuitry 50 may determine the threshold value and/or the baseline value based on posture information. For instance, processing circuitry 50 may assign a respective threshold value and/or baseline value to each posture of a set of postures (e.g., postures, such as supine, left-lateral, right-lateral, or prone).

Figure 7:
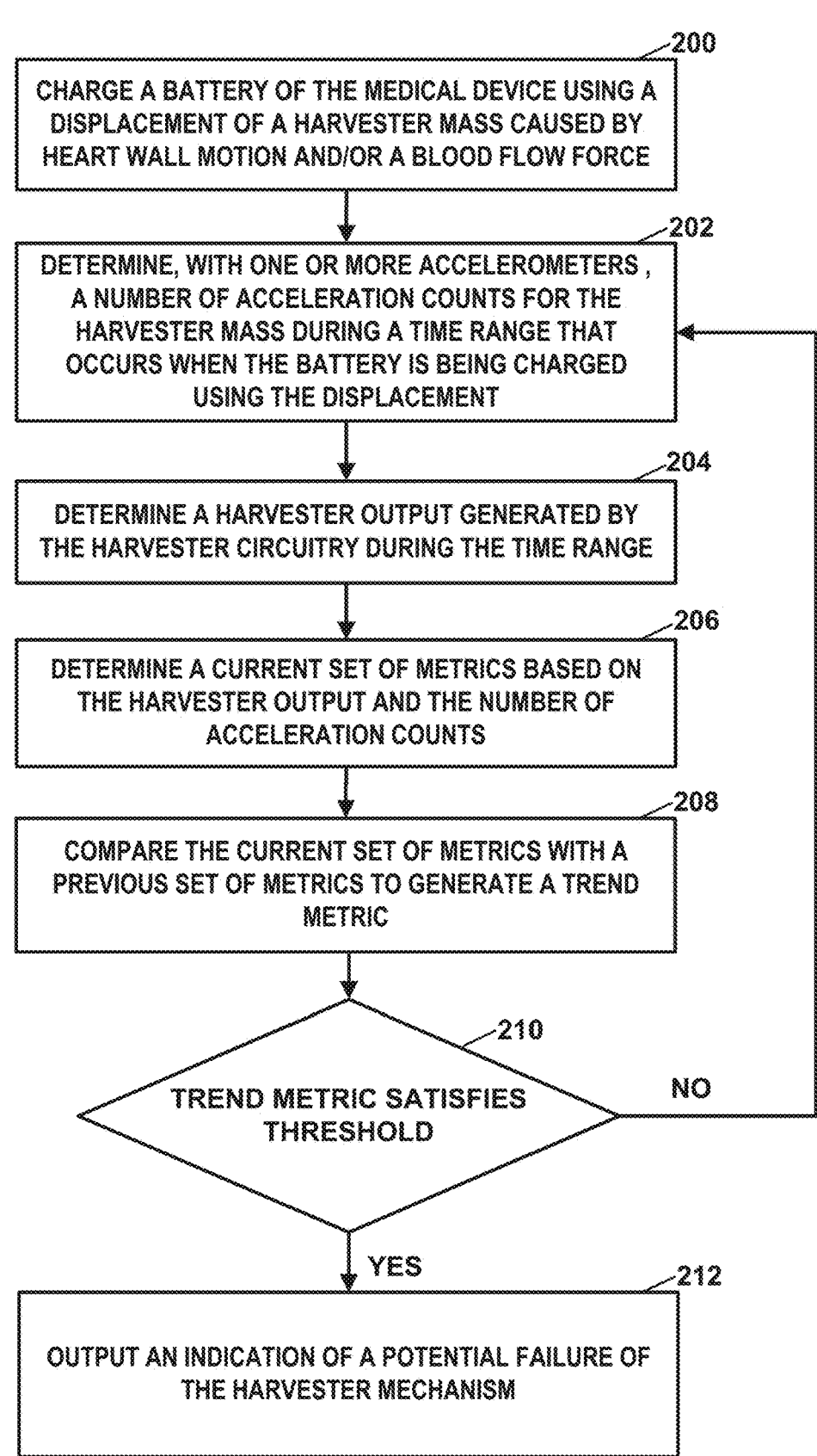
FIG. 7 is a flow diagram illustrating an example operation of determining a trend metric in accordance with the techniques of the disclosure.

FIG. 7 is a flow diagram illustrating an example operation of determining a trend metric in accordance with the techniques of the disclosure. FIG. 7 is discussed with FIGS. 1-6 for example purposes only. In accordance with the techniques of the disclosure, harvester circuitry 55 may charge battery 61 of medical device 10 using a displacement of harvester mass 57 caused by heart wall motion and/or blood flow forces (200). Processing circuitry 50 may determine, with the one or more accelerometers 60, a number of acceleration counts for harvester mass 57 during a time range that occurs when harvester circuitry 55 charges battery 61 using the displacement of harvester mass 57 (202). Processing circuitry 50 may determine the number of acceleration counts as an integral sum of acceleration of medical device 10 over time.

In some examples, processing circuitry 50 may determine the number of acceleration counts based on posture information for the patient. For instance, processing circuitry 50 may determine the number of acceleration counts to count each acceleration count that is associated with a posture indicated by the posture information for the patient and to refrain from counting acceleration counts that are associated with a posture different from the posture indicated by the posture information for the patient. Processing circuitry 50 may determine the number of acceleration counts based on a time of day. For instance, processing circuitry 50 may determine the number of acceleration counts to count each acceleration count that occurs during a first time range (e.g., night) and to refrain from counting acceleration counts that occur during a second time range (e.g., daytime).

Processing circuitry 50 may filter an output of one or more accelerometers 60. For example, processing circuitry 50 may filter an output of one or more accelerometers 60 using a band pass filter corresponding to 10 Hz to 30 Hz. In some examples, processing circuitry 50 may filter an output of one or more accelerometers 60 using a natural frequency of harvester mass 57. Processing circuitry 50 may filter an output of one or more accelerometers 60 to comprise a single vector corresponding to a single direction of acceleration of harvester mass 57.

Processing circuitry 50 may determine a harvester output generated by harvester circuitry 55 during the time range (204). The harvester output may include a power generated by harvester circuitry 55 using the displacement of harvester mass 57 during the time range that occurs when harvester circuitry 55 charges the battery using the displacement of harvester mass 57. Processing circuitry 50 may determine a current set of metrics based on the harvester output to the number of acceleration counts (206). Processing circuitry 50 may compare the current set of metrics with a previous set of metrics to generate a trend metric (208). For example, processing circuitry 50 may determine a first polynomial expression based on the previous set of metrics. For instance, processing circuitry 50 may apply linear regression on the previous set of metrics. Processing circuitry 50 may determine the previous set of metrics based on posture information. For instance, processing circuitry 50 may assign each previous set of metrics to a respective posture of a set of postures (e.g., postures (e.g., supine, left-lateral, right-lateral, or prone). In this instance, processing circuitry 50 may select the previous set of metrics that corresponds to (e.g., matches) a posture indicated by posture information.

In this example, processing circuitry 50 may determine a second polynomial expression based on the current set of metrics. For instance, processing circuitry 50 may apply linear regression on the current set of metrics. Processing circuitry 50 may compare the first polynomial expression and the second polynomial expression to generate the trend metric.

Processing circuitry 50 may determine whether the trend metric satisfies a threshold value (210). In response to a determination that the trend metric does not satisfy the threshold value ("NO" of step 210), the process returns to step 202. In response, however, to a determination that the trend metric satisfies the threshold value ("YES" of step 210), processing circuitry 50 may output an indication of a potential failure of the harvester mechanism (212).

For example, processing circuitry 50 may, in response to a determination that the second polynomial expression indicates a smaller slope than the first polynomial expression by at least a threshold value, determine that the potential failure has occurred at the harvester mechanism. Processing circuitry 50 may output an instruction to cause external device 12 to output the indication of the potential failure of the harvester mechanism. In some examples, processing circuitry 50 may output an instruction to cause a physician device (e.g., computing system 24) to output the indication of the potential failure of the harvester mechanism.

FIG. 8 is a flow diagram illustrating an example operation of outputting an indication of a potential failure of a harvester mechanism in accordance with the techniques of the disclosure. FIG. 8 is discussed with FIGS. 1-7 for example purposes only. In accordance with the techniques of the disclosure, processing circuitry 50 may determine, with the one or more accelerometers 60, motion information for harvester mass 57 during a time range that occurs when harvester circuitry 55 charges battery 61 using the displacement of harvester mass 57 (302). For example, processing circuitry 50 may determine, with one or more accelerometers 60, a number of acceleration counts for harvester mass 57 during a time range that occurs when harvester circuitry 55 charges battery 61 using the displacement of harvester mass 57. Processing circuitry 50 may determine the number of acceleration counts as an integral sum of acceleration of medical device 10 over time.

In some examples, processing circuitry 50 may determine the motion information based on posture information for the patient. For instance, processing circuitry 50 may determine a number of acceleration counts to count each acceleration count that is associated with a posture indicated by the posture information for the patient and to refrain from counting acceleration counts that are associated with a posture different from the posture indicated by the posture information for the patient. Processing circuitry 50 may determine the number of acceleration counts based on a time of day. For instance, processing circuitry 50 may determine the number of acceleration counts to count each acceleration count that occurs during a first time range (e.g., night) and to refrain from counting acceleration counts that occur during a second time range (e.g., daytime).

In some examples, processing circuitry 50 may filter an output of one or more accelerometers 60. For example, processing circuitry 50 may filter an output of one or more accelerometers 60 using a band pass filter corresponding to 10 Hz to 30 Hz. In some examples, processing circuitry 50 may filter an output of one or more accelerometers 60 using a natural frequency of harvester mass 57. Processing circuitry 50 may filter an output of one or more accelerometers 60 to comprise a single vector corresponding to a single direction of acceleration of harvester mass 57. Processing circuitry 50 may determine a harvester output generated by harvester circuitry 55 during the time range (304). The harvester output may include a power generated by harvester circuitry 55 using the displacement of harvester mass 57 during the time range that occurs when harvester circuitry 55 charges the battery using the displacement of harvester mass 57.

Processing circuitry 50 may output an indication of a potential failure of the harvester mechanism based on the motion information and the harvester output (306). Processing circuitry 50 may output an instruction to cause external device 12 to output the indication of the potential failure of the harvester mechanism. In some examples, processing circuitry 50 may output an instruction to cause a physician device (e.g., computing system 24) to output the indication of the potential failure of the harvester mechanism.

For example, processing circuitry 50 may determine a ratio value for the time range based on a ratio of the harvester output to a number of acceleration counts and output an indication of a potential failure of the harvester mechanism in response to a determination that the ratio value satisfies a threshold value (see FIG. 6). In some examples, processing circuitry 50 may determine a current set of metrics based on the harvester output to a number of acceleration counts and compare the current set of metrics with a previous set of metrics to generate a trend metric. In this example, processing circuitry 50 may output an indication of a potential failure of the harvester mechanism based on the trend metric (see FIG. 7).

In some examples, when a problem in the harvesting mechanism is detected, IMD 10 may be configured to start conserving power by turning off one or more features. For example, processing circuitry 50 may reduce a power usage by IMD 10 based on the motion information and the harvester output. For instance, processing circuitry 50 may determine that a potential failure of the harvester mechanism has occurred based on the motion information and the harvester and, in response to a determination that the potential failure of the harvester mechanism has occurred, reduce a power usage by the IMD 10.

For example, processing circuitry 50 may determine a ratio value for the time range based on a ratio of the harvester output to a number of acceleration counts and reduce a power usage by IMD 10 in response to a determination that the ratio value satisfies a threshold value (see FIG. 6). In some instances, processing circuitry 50 may determine a current set of metrics based on the harvester output to a number of acceleration counts and compare the current set of metrics with a previous set of metrics to generate a trend metric. In this instance, processing circuitry 50 may reduce a power usage by IMD 10 based on the trend metric (see FIG. 7). To reduce the power usage by IMD 10, processing circuity 50 may turn off one or more of activity sensing, a rate response, atrioventricular (AV) synchrony, or switch from dual-chamber to single-chamber pacing, or reduce to a lower pacing rate.

In some examples, the techniques of the disclosure include a system that comprises means to perform any method described herein. In some examples, the techniques of the disclosure include a computer-readable medium comprising instructions that cause processing circuitry to perform any method described herein.

The following clauses are a non-limiting list of examples in accordance with one or more techniques of this disclosure.

Clause 1. A system comprising: harvester circuitry configured to charge a battery for a medical device using a displacement of a harvester mass; one or more accelerometers configured to detect a motion associated with the harvester mass; and processing circuitry configured to: determine, with the one or more accelerometers, motion information for the implanted medical device during a time range that occurs when the harvester circuitry charges the battery using the displacement of the harvester mass; determine a harvester output generated by the harvester circuitry during the time range; and output an indication of a potential failure of the harvester mechanism based on the motion information and the harvester output.

Clause 2. The system of clause 1, wherein the processing circuitry is configured to: determine a ratio value for the time range based on the harvester output and the motion information; and wherein the processing circuitry is configured to output the indication of the potential failure in response to a determination that the ratio value satisfies a threshold value.

Clause 3. The system of clause 2, wherein the motion information indicates a number of acceleration counts; and wherein, to determine the ratio value, the processing circuitry is configured to determine the ratio value for the time range as a ratio of the harvester output to the acceleration counts.

Clause 4. The system of any of clauses 2-3, wherein the processing circuitry is further configured to determine the threshold value based on posture information for the patient.

Clause 5. The system of any of clauses 1-4, wherein the processing circuitry is configured to determine the motion information based on posture information for the patient.

Clause 6. The system of any of clauses 4-5, wherein the processing circuitry is further configured to determine the posture information for the patient using the one or more accelerometers.

Clause 7. The system of clause 1, wherein the motion information indicates a number of acceleration counts and wherein the processing circuitry is configured to: determine a current set of metrics based on the harvester output and the number of acceleration counts; compare the current set of metrics with a previous set of metrics to generate a trend metric; and output the indication of the potential failure based on the trend metric.

Clause 8. The system of clause 7, wherein, to compare the current set of metrics with the previous set of metrics, the processing circuitry is configured to: determine a first polynomial expression based on the previous set of metrics; determine a second polynomial expression based on the current set of metrics; and compare the first polynomial expression and the second polynomial expression to generate the trend metric.

Clause 9. The system of clause 8, wherein, to determine the first polynomial expression, the processing circuitry is configured to apply linear regression to the previous set of metrics; and wherein, to determine the second polynomial expression, the processing circuitry is configured to apply linear regression the current set of metrics.

Clause 10. The system of clause 9, wherein, to compare the current set of metrics with the previous set of metrics, the processing circuitry is configured to: in response to a determination that the second polynomial expression indicates a smaller slope than the first polynomial expression by at least a threshold value, determine that the potential failure has occurred at the harvester mechanism.

Clause 11. The system of any of clauses 7-10, wherein the processing circuitry is further configured to determine the previous set of metrics based on posture information for the patient.

Clause 12. The system of clause 11, wherein the processing circuitry is further configured to determine the posture information for the patient using the one or more accelerometers.

Clause 13. The system of any of clauses 7-11, wherein the processing circuitry is configured to determine the number of acceleration counts as an integral sum of acceleration over time.

Clause 14. The system of any of clauses 1-13, wherein, to determine the motion information, the processing circuitry is configured to filter an output of the one or more accelerometers using a band pass filter corresponding to 10 Hz to 30 Hz.

Clause 15. The system of any of clauses 1-14, wherein, to determine the motion information, the processing circuitry is configured to filter an output of the one or more accelerometers using a natural frequency of the harvester mass.

Clause 16. The system of any of clauses 1-15, wherein, to determine the motion information, the processing circuitry is configured to filter an output of the one or more accelerometers to comprise a single vector corresponding to a single direction of acceleration of the harvester mass.

Clause 17. The system of any of clauses 1-16, wherein the harvester mass is configured to translate a heart wall motion and/or a blood flow force into the displacement of the harvester mass.

Clause 18. The system of any of clauses 1-17, wherein, to output the indication of the potential failure of the harvester mechanism, the processing circuitry is configured to output an instruction to cause an external device to output the indication of the potential failure of the harvester mechanism.

Clause 19. The system of any of clauses 1-18, wherein, to output the indication of the potential failure of the harvester mechanism, the processing circuitry is configured to output an instruction to cause a physician device to output the indication of the potential failure of the harvester mechanism.

Clause 20. The system of any of clauses 1-19, wherein the processing circuitry is configured to: determine the motion information based on a time of day; and determine the harvester output based on the time of day.

Clause 21. The system of any of clauses 1-20, wherein the medical device comprises an implantable medical device.

Clause 22. The system of clause 21, wherein the one or more accelerometers are arranged in the implantable medical device and configured to determine a motion of the medical device while implanted in the patient.

Clause 23. The system of any of clauses 1-22, further comprising the harvester mass, wherein the harvester mass arranged in the medical device.

Clause 24. The system of any of clauses 1-23, further comprising: telemetry circuitry configured for communication between the medical device and an external device associated with the medical device; and wherein the processing circuitry is arranged in the external device.

Clause 25. The system of any of clauses 1-23, wherein the processing circuitry is arranged in the medical device.

Clause 26. The system of any of clauses 1-25, wherein the harvester output comprises a power generated using the displacement of the harvester mass during the time range that occurs when the harvester circuitry charges the battery using the displacement of the harvester mass.

Clause 27. The system of any of clauses 1-26, wherein the medical device is configured to provide a therapy to a heart of the patient for a treatment of one or more of arrhythmia, cardiac arrest, bradycardia, myocardial infarction, stroke, or seizure.

Clause 28. The system of any of clauses 1-27, wherein the medical device comprises a pacemaker or an implantable cardioverter-defibrillator.

Clause 29. The system of any of clauses 1-28, wherein the harvester output comprises one or more of a power, a voltage, a current, or an energy generated using the displacement of the harvester mass during the time range.

Clause 30. The system of any of clauses 1-29, wherein the processing circuitry is configured to: determine that a potential failure of the harvester mechanism has occurred based on the motion information and the harvester; and in response to the determination that the potential failure of the harvester mechanism has occurred, reduce a power usage by the medical device.

Clause 31. A method comprising: determining, by processing circuitry and with one or more accelerometers, motion information for an implanted medical device during a time range that occurs when harvester circuitry charges a battery using a displacement of the harvester mass; determining, by the processing circuitry, a harvester output generated by the harvester circuitry during the time range; and outputting, by the processing circuitry, an indication of a potential failure of the harvester mechanism based on the motion information and the harvester output.

Clause 32. The method of clause 31, further comprising: determining, by the processing circuitry, a ratio value for the time range based on the harvester output and the motion information; and wherein the outputting of the indication of the potential failure is in response to a determination that the ratio value satisfies a threshold value.

Clause 33. The method of clause 32, wherein the motion information indicates a number of acceleration counts; and wherein determining the ratio value comprises determining the ratio value for the time range as a ratio of the harvester output to the acceleration counts.

Clause 34. The method of any of clauses 32-33, further comprising determining, by the processing circuitry, the threshold value based on posture information for the patient.

Clause 35. The method of any of clauses 31-34, further comprising determining, by the processing circuitry, the motion information based on posture information for the patient.

Clause 36. The method of any of clauses 34-35, further comprising determining, by the processing circuitry, the posture information for the patient using the one or more accelerometers.

Clause 37. The method of clause 31, wherein the motion information indicates a number of acceleration counts, the method further comprising: determining, by the processing circuitry, a current set of metrics based on the harvester output and the number of acceleration counts; comparing, by the processing circuitry, the current set of metrics with a previous set of metrics to generate a trend metric; and outputting, by the processing circuitry, the indication of the potential failure based on the trend metric.

Clause 38. The method of clause 37, wherein comparing the current set of metrics with the previous set of metrics comprises: determining a first polynomial expression based on the previous set of metrics; determining a second polynomial expression based on the current set of metrics; and comparing the first polynomial expression and the second polynomial expression to generate the trend metric.

Clause 39. The method of clause 38, wherein determining the first polynomial expression comprises applying linear regression to the previous set of metrics; and wherein determining the second polynomial expression comprises applying linear regression the current set of metrics.

Clause 40. The method of clause 39, wherein comparing the current set of metrics with the previous set of metrics comprises: in response to determining that the second polynomial expression indicates a smaller slope than the first polynomial expression by at least a threshold value, determining that the potential failure has occurred at the harvester mechanism.

Clause 41. The method of any of clauses 37-40, further comprising determining, by the processing circuitry, the previous set of metrics based on posture information for the patient.

Clause 42. The method of clause 41, further comprising determining the posture information for the patient using the one or more accelerometers.

Clause 43. The method of any of clauses 37-41, further comprising determining, by the processing circuitry, the number of acceleration counts as an integral sum of acceleration over time.

Clause 44. The method of any of clauses 31-43, wherein determining the motion information comprises filtering an output of the one or more accelerometers using a band pass filter corresponding to 10 Hz to 30 Hz.

Clause 45. The method of any of clauses 31-44, wherein determining the motion information comprises filtering an output of the one or more accelerometers using a natural frequency of the harvester mass.

Clause 46. The method of any of clauses 31-45, wherein determining the motion information comprises filtering an output of the one or more accelerometers to comprise a single vector corresponding to a single direction of acceleration of the harvester mass.

Clause 47. The method of any of clauses 31-46, wherein the harvester mass is configured to translate a heart wall motion and/or a blood flow force into the displacement of the harvester mass.

Clause 48. The method of any of clauses 31-47, wherein outputting the indication of the potential failure of the harvester mechanism comprises outputting an instruction to cause an external device to output the indication of the potential failure of the harvester mechanism.

Clause 49. The method of any of clauses 31-48, wherein outputting the indication of the potential failure of the harvester mechanism comprises outputting an instruction to cause a physician device to output the indication of the potential failure of the harvester mechanism.

Clause 50. The method of any of clauses 31-49, further comprising: determining, by the processing circuitry, the motion information based on a time of day; and determining, by the processing circuitry, the harvester output based on the time of day.

Clause 51. The method of any of clauses 31-50, wherein the medical device comprises an implantable medical device.

Clause 52. The method of clause 51, wherein the one or more accelerometers are arranged in the implantable medical device and configured to determine a motion of the medical device while implanted in the patient.

Clause 53. The method of any of clauses 31-52, further comprising the medical device.

Clause 54. The method of any of clauses 31-53, wherein the harvester mass arranged in the medical device.

Clause 55. The method of any of clauses 31-54, wherein telemetry circuitry configured for communication between the medical device and an external device associated with the medical device is arranged in the medical device; and wherein the processing circuitry is arranged in the external device.

Clause 56. The method of any of clauses 31-54, wherein the processing circuitry is arranged in the medical device.

Clause 57. The method of any of clauses 31-56, wherein the harvester output comprises a power generated using the displacement of the harvester mass during the time range that occurs when the harvester circuitry charges the battery using the displacement of the harvester mass.

Clause 58. The method of any of clauses 31-57, wherein the medical device is configured to provide a therapy to a heart of the patient for a treatment of one or more of arrhythmia, cardiac arrest, bradycardia, myocardial infarction, stroke, or seizure.

Clause 59. The method of any of clauses 31-57, wherein the medical device comprises a pacemaker or an implantable cardioverter-defibrillator.

Clause 60. The method of any of clauses 31-58, wherein the harvester output comprises one or more of a power, a voltage, a current, or an energy generated using the displacement of the harvester mass during the time range.

Clause 61. The method of any of clauses 31-60, further comprising: determining, by the processing circuitry, that a potential failure of the harvester mechanism has occurred based on the motion information and the harvester; and in response to determining that the potential failure of the harvester mechanism has occurred, reducing, by the processing circuitry, a power usage by the medical device.

Clause 62. A medical device comprising: harvester circuitry configured to charge a battery for the medical device using a displacement of a harvester mass; one or more accelerometers configured to detect a motion of the medical device; telemetry circuitry configured for communication; and processing circuitry configured to: determine, with the one or more accelerometers, motion information for the implanted medical device during a time range that occurs when the harvester circuitry charges the battery using the displacement of the harvester mass; determine a harvester output generated by the harvester circuitry during the time range; and output an indication of a potential failure of the harvester mechanism based on the motion information and the harvester output.

Various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

Various examples have been described. These and other examples are within the scope of the following claims.

What is claimed is:

1. A system comprising:
a harvester mechanism comprising harvester circuitry and a harvester mass, wherein the harvester circuitry is configured to charge a battery for a medical device using a displacement of the harvester mass;
one or more accelerometers configured to detect a motion associated with the harvester mass; and
processing circuitry configured to:
determine, with the one or more accelerometers, motion information for the implanted medical device during a time range that occurs when the harvester circuitry charges the battery using the displacement of the harvester mass;
determine a harvester output generated by the harvester circuitry during the time range; and
modify a power usage by the medical device based on an indication of a potential failure of the harvester mechanism, wherein the indication of the potential failure is based on the motion information and the harvester output.

2. The system of claim 1, wherein the processing circuitry is configured to:
determine a ratio value for the time range based on the harvester output and the motion information; and
wherein the processing circuitry is configured to output the indication of the potential failure in response to a determination that the ratio value satisfies a threshold value.

3. The system of claim 2,
wherein the motion information indicates a number of acceleration counts; and
wherein, to determine the ratio value, the processing circuitry is configured to determine the ratio value for the time range as a ratio of the harvester output to the acceleration counts.

4. The system of claim 2, wherein the processing circuitry is further configured to determine the threshold value based on posture information for a patient having the medical device.

5. The system of claim 1, wherein the processing circuitry is configured to determine the motion information based on posture information for a patient having the medical device.

6. The system of claim 5, wherein the processing circuitry is further configured to determine the posture information for the patient using the one or more accelerometers.

7. The system of claim 1, wherein the motion information indicates a number of acceleration counts and wherein the processing circuitry is configured to:

determine a current set of metrics based on the harvester output and the number of acceleration counts;

compare the current set of metrics with a previous set of metrics to generate a trend metric; and output the indication of the potential failure based on the trend metric.

8. The system of claim 7, wherein, to compare the current set of metrics with the previous set of metrics, the processing circuitry is configured to:

determine a first polynomial expression based on the previous set of metrics;

determine a second polynomial expression based on the current set of metrics; and compare the first polynomial expression and the second polynomial expression to generate the trend metric.

9. The system of claim 8, wherein, to determine the first polynomial expression, the processing circuitry is configured to apply linear regression to the previous set of metrics; and wherein, to determine the second polynomial expression, the processing circuitry is configured to apply linear regression to the current set of metrics.

10. The system of claim 9, wherein, to compare the current set of metrics with the previous set of metrics, the processing circuitry is configured to:

in response to a determination that the second polynomial expression indicates a smaller slope than the first polynomial expression by at least a threshold value, determine that the potential failure has occurred at the harvester mechanism.

11. The system of claim 7, wherein the processing circuitry is further configured to determine the previous set of metrics based on posture information for a patient having the medical device.

12. The system of claim 11, wherein the processing circuitry is further configured to determine the posture information for the patient using the one or more accelerometers.

13. The system of claim 7, wherein the processing circuitry is configured to determine the number of acceleration counts as an integral sum of acceleration over time.

14. The system of claim 1, wherein, to determine the motion information, the processing circuitry is configured to filter an output of the one or more accelerometers using a band pass filter corresponding to 10 Hz to 30 Hz.

15. The system of claim 1, wherein, to determine the motion information, the processing circuitry is configured to filter an output of the one or more accelerometers using a natural frequency of the harvester mass.

16. The system of claim 1, wherein, to determine the motion information, the processing circuitry is configured to filter an output of the one or more accelerometers to comprise a single vector corresponding to a single direction of acceleration of the harvester mass.

17. The system of claim 1, wherein the harvester mass is configured to translate a heart wall motion and/or a blood flow force into the displacement of the harvester mass.

18. The system of claim 1, wherein the processing circuitry is configured to output an instruction to cause an external device to output the indication of the potential failure of the harvester mechanism.

19. The system of claim 1, wherein, to modify the power usage by the medical device, the processing circuitry is configured to reduce the power usage by the medical device by turning off one or more features of the medical device.

20. A method of monitoring a harvester mechanism comprising harvester circuitry and a harvester mass, the method comprising:

determining, by processing circuitry and with one or more accelerometers, motion information for an implanted medical device during a time range that occurs when the harvester circuitry charges a battery using a displacement of the harvester mass;

determining, by the processing circuitry, a harvester output generated by the harvester circuitry during the time range; and modifying, by the processing circuitry, a power usage by the medical device based on an indication of a potential failure of the harvester mechanism, wherein the indication of the potential failure is based on the motion information and the harvester output.

21. A medical device comprising:

a harvester mechanism comprising harvester circuitry and a harvester mass, wherein the harvester circuitry is configured to charge a battery for the medical device using a displacement of the harvester mass;

one or more accelerometers configured to detect a motion of the medical device;

telemetry circuitry configured for communication; and processing circuitry configured to:

determine, with the one or more accelerometers, motion information for the unplanted medical device during a time range that occurs when the harvester circuitry charges the battery using the displacement of the harvester mass;

determine a harvester output generated by the harvester circuitry during the time range; and modify a power usage by the medical device based on an indication of a potential failure of the harvester mechanism, wherein the indication of the potential failure is based on the motion information and the harvester output.

* * * * *